(12) United States Patent
Naumann et al.

(10) Patent No.: US 7,198,648 B2
(45) Date of Patent: Apr. 3, 2007

(54) COUPLING COMPONENT FOR OXIDATIVE HAIR DYES

(75) Inventors: Frank Naumann, Duesseldorf (DE); Astrid Kleen, Erkrath (DE); Horst Hoeffkes, Duesseldorf (DE); Bernd Meinigke, Leverkusen (DE)

(73) Assignee: Henkel Kommanditgesellschaft Auf Aktien (Henkel KGAA), Duesseldorf (DE)

( * ) Notice: Subject to any disclaimer, the term of this patent is extended or adjusted under 35 U.S.C. 154(b) by 554 days.

(21) Appl. No.: 10/297,871

(22) PCT Filed: Jun. 9, 2001

(86) PCT No.: PCT/EP01/06556

§ 371 (c)(1),
(2), (4) Date: Dec. 9, 2002

(87) PCT Pub. No.: WO01/97756

PCT Pub. Date: Dec. 27, 2001

(65) Prior Publication Data

US 2003/0167578 A1    Sep. 11, 2003

(30) Foreign Application Priority Data

Jun. 20, 2000  (DE) ................................. 100 30 313
Apr. 26, 2001  (DE) ................................. 101 20 307

(51) Int. Cl.
*A61K 7/13* (2006.01)

(52) U.S. Cl. ........................ 8/405; 8/406; 8/409; 8/421; 8/568; 132/202; 132/208; 546/249

(58) Field of Classification Search .................... 8/405, 8/406, 409, 421, 568; 546/249; 132/202, 132/208

See application file for complete search history.

(56) References Cited

U.S. PATENT DOCUMENTS

| | | | |
|---|---|---|---|
| 4,003,699 A | 1/1977 | Rose et al. | |
| 4,210,654 A | 7/1980 | Bauer et al. | |
| 4,865,774 A | 9/1989 | Fabry et al. | |
| 4,931,218 A | 6/1990 | Schenker et al. | |
| 5,061,289 A | 10/1991 | Clausen et al. | |
| 5,078,750 A * | 1/1992 | Komai et al. | |
| 5,294,726 A | 3/1994 | Behler et al. | |
| 5,380,340 A | 1/1995 | Neunhoeffer et al. | |
| 5,534,267 A | 7/1996 | Neunhoeffer et al. | |
| 5,538,517 A * | 7/1996 | Samain et al. .................. | 8/423 |
| 5,612,024 A * | 3/1997 | Giede et al. ............. | 424/70.11 |
| 5,663,366 A | 9/1997 | Neunhoeffer et al. | |
| 5,681,554 A * | 10/1997 | Cannell et al. .......... | 424/70.14 |
| 5,766,576 A | 6/1998 | Löwe et al. | |
| 6,090,161 A | 7/2000 | Hoeffkes et al. | |
| 6,099,592 A | 8/2000 | Vidal et al. | |
| 6,146,429 A * | 11/2000 | Gast et al. ..................... | 8/408 |
| 6,284,003 B1 | 9/2001 | Rose et al. | |
| 6,369,042 B1 * | 4/2002 | Oberthür et al. | |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| DE | 199 55 915 A1 | 6/2001 |
| EP | 0001079 | 3/1979 |
| EP | 0 678 293 A2 | 10/1995 |
| EP | 0 740 931 B1 | 8/1997 |
| EP | 0 873 744 A2 | 10/1998 |
| EP | 1 101 823 A2 | 5/2001 |
| GB | 1 026 978 | 4/1966 |
| JP | 62-132813 | 6/1987 |

(Continued)

OTHER PUBLICATIONS

English Abstract of Japanese Patent No. 63014712 A (STIC Search Report, pp. 38-39) .*
English Abstract of Japanese Patent No. 06183934A.*
English Abstract of Japanese No. 62132814 A (STIC Search Report, p. 40) .*
Chemical Abstracts vol. 107 No. 20 Abstract No. 183330 of JP 62 132813 (1987) XP002183446.
Chemical Abstracts vol. 112 No. 8 Abstract No. 62357 of JP 066109 (1989) XP002184004.

(Continued)

*Primary Examiner*—Eisa Elhilo
(74) *Attorney, Agent, or Firm*—Woodcock Washburn LLP

(57) ABSTRACT

The invention relates to a method for dyeing keratin fibers, especially human hair. The inventive method comprises the following steps: optionally applying a pretreatment agent M1 to the fiber, using a dye M2 on the fiber which is optionally mixed immediately before application to the fiber from a component M2a, containing at least one oxidative dye pre-product of the developer type and/or an indole and/or indole derivative and a component M2b, containing an oxidative dye and/or an enzyme. If desired, a third agent M3 is added to the individual agents M2a or M2b before mixing them or to the mixture M2, and said dye M2 is rinsed from the fiber after a period of 5–10 minutes. At least one of the agents M1, M2a, M2b or M3 contains a compound from the vitamin B6 group. The invention further relates to hair pretreatment agents, to agents for dyeing keratin fibers, to their packing in corresponding kits and to the use thereof. The inventive compounds of the vitamin B6 group and their physiologically acceptable salts are useful as coupling components in the production of oxidative dyes that contain conventional developer and/or coupling compounds and/or indole and/or indole derivatives in a substrate appropriate for dyeing. The inventive compounds are further useful as active substances that improve the hair structure.

7 Claims, No Drawings

FOREIGN PATENT DOCUMENTS

| | | |
|---|---|---|
| JP | 62-132814 | 6/1987 |
| JP | 63-014712 | 1/1988 |
| JP | 64-066109 | 3/1989 |
| JP | 02-019576 | 1/1990 |
| JP | 06-183934 | 7/1994 |
| WO | WO 94/08969 A1 | 4/1994 |
| WO | WO 94/08970 A1 | 4/1994 |
| WO | WO 96 15765 A1 | 5/1996 |
| WO | WO 96/25943 * | 8/1996 |
| WO | WO 99/06016 A1 | 2/1999 |

OTHER PUBLICATIONS

Chemical Abstracts vol. 107 No. 20 Abstract No. 183331 of JP 62 132814 (1987) XP002184002.

Chemical Abstracts vol. 110 No. 114 Abstract No. 121002 of JP 63 014712 (1988) XP002184003.

Patent Abstracts of Japan. vol. 0185, No. 28 of JP 0168394 (1989).

Schrader. Grundlagen und Rezepturen der Kosmetika. vol. 2. Huthig Buch Vergla Heidelberg. (1989).

F. Schwenker et al "Differential Thermal Analysis of Protein Fibers". Textile Research Institut Princeton. New Jersey vol. 30. p. 800-801 (1960).

W. D. Felix et al., The Differential Thermal Analysis of Natural and Modified Wool and Mohair vol. 33. p. 465 (1963) F J Wortmann et al. Characterizing Keratins Using High-Pressure Differential Scann Calorimetry (HPDSC). Journal of Applied Polymer Science. vol. 48. pp. 137-150 (1993).

\* cited by examiner

COUPLING COMPONENT FOR OXIDATIVE HAIR DYES

CROSS REFERENCE TO RELATED APPLICATIONS

This application is a national stage application under 35 U.S.C. §371 of international application PCT/EP01/06556 filed on Jun. 9, 2001, the international application not being published in English. This application also claims priority under 35 U.S.C. 119 to DE 100 30 313.7 filed Jun. 20, 2000

BACKGROUND OF THE INVENTION

This invention relates to processes for coloring keratin fibers in which at least one pyridoxine, pyridoxal or pyridoxamine derivative is used, to colorants containing such compounds and to kits for use in the process according to the invention.

Keratin fibers in the context of the invention are understood to include pelts, wool, feathers and, in particular, human hair. Nowadays, human hair is treated in many different ways with hair-care preparations. Such treatments include, for example, the cleaning of hair with shampoos, the care and regeneration of hair with rinses and conditioners and the bleaching, coloring and shaping of hair with coloring and tinting formulations, wave formulations and styling preparations. Among these, formulations for modifying or shading the color of the hair play a prominent role.

Colorants or tints containing substantive dyes as their coloring component are normally used for temporary colors. Substantive dyes are based on dye molecules which are directly absorbed onto the hair and do not require an oxidative process for developing the color. Dyes such as these include, for example, henna which has been used since ancient times for coloring the body and hair. Corresponding colors are generally sensitive to shampooing so that an often unwanted change of shade or even a visible "decoloration" can occur.

By virtue of their intensive colors and good fastness properties which are achieved at relatively low coloring temperatures and in short coloring times, so-called oxidation colorants play a particular role in the coloring of keratin fibers, especially hair. Oxidation colorants contain a primary intermediate in a suitable, generally water-containing carrier. This primary intermediate forms the dye by oxidative coupling under the influence of atmospheric oxygen or oxidizing agents. The dye can be intensified and modified in shade by coupling with another primary intermediate or with so-called secondary intermediates which are not themselves able to form dyes.

Good oxidation dye precursors are expected to satisfy above all the following requirements: they must form the required color tones with sufficient intensity and fastness during the oxidative coupling reaction. In addition, they must be readily absorbed onto the fibers with no significant differences—particularly in the case of human hair—between damaged and freshly regrown hair (levelling behavior). They are expected to be fast to light, heat and the effect of chemical reducing agents, for example permanent wave lotions. Finally, if they are used to color hair, they should not overly stain the scalp and, above all, should be toxicologically and dermatologically safe. In addition, the color obtained, for example by blonding, should be easily removable from the hair if it does not meet the individual wishes of the user and is to be taken out.

Users of hair colorants seek inter alia to achieve a natural-looking hair color as the outcome of the coloring process. This is the case above all when gray hair is to be inconspicuously hidden by a natural-looking color. When it comes to obtaining natural-looking shades, considerable significance attaches to hair coloring and tinting formulations which color in shades of the red and brown range. Oxidation colorants in the red and brown range which are available, for example, in the combination of 2,4,5,6-tetraaminopyrimidine with 2-methyl resorcinol are not yet optimal in regard to the uniformity with which the color is absorbed. Golden tones have not yet been satisfactorily obtainable using conventional combinations of primary and secondary intermediates. In order to obtain a broad range of tones, substantive dyes inter alia may be used for shading. Substantive dyes are generally not fast to washing and, because of this, are not so suitable for combination with oxidation dyes.

A natural-looking hair color also comes from a coloring process where indole or indoline derivatives are used as precursors of so-called "nature-analogous" dyes in the hair colorant applied. According to WO 9906016 A1, partly or completely gray hair can be colored back to its original natural shade by using a combination of derivatives of indole or indoline with typical secondary intermediates, so that no significant difference from any naturally pigmented hair still present is visible. Blond to mid-brown colors are obtained. The dye combinations disclosed in WO 9906016 A1 give dark to black colors with no red which were always difficult to obtain with the traditional primary/secondary intermediate combinations.

The coloring of keratin fibers using "nature-analogous" dyes is setting a trend of achieving natural-looking colors even with natural or "nature-identical" dye precursors. Accordingly, it is desirable to be able to vary the color of the hair by adding an equally natural or "nature-identical" oxidation dye precursor of the secondary intermediate type. Access to a broader range of colors should thus be gained and an intensive color fast to washing and light obtained.

Besides optimizing the coloring effect of hair colorants, improving their compatibility is another problem to be addressed. Oxidative components, for example in hair colorants, have a damaging effect on the structure of hair keratin. The hair undergoes a weight loss and a measurable reduction in the denaturing temperature of the keratin. Increasing fragility, reduced combability of the hair and a deterioration in the body and hold of the hair are the outcome. In addition, structurally damaged hair has a dull, lackluster appearance. These problems should be counteracted with structure-improving additives in the coloring process, advantageously as constituents of the colorant itself.

For these reasons, there is a need for new oxidation dye precursors and active care ingredients which would enable the parameters mentioned to be improved, It has surprisingly been found that pyridoxine, pyridoxal or pyridoxamine derivatives excellently satisfy the requirements stated above.

Pyridoxine and other compounds of the vitamin B6 group have been mentioned as components in hair tonics for reducing refatting and for stimulating hair growth. EP 0678293 A2 proposes topical compositions containing pyridoxine tripropionate for treating the hair and skin. EP 001079 A1 describes anti-seborrheic cosmetic compositions containing pyridoxine tripalmitate as their active ingredient.

EP 873744 A2 describes carbonyl compounds, inter alia pyridoxal, in combination with amines, hydroxy compounds, peptides, CH-active compounds and other components as dye precursors in preferably non-oxidative hair colorants.

Hair colorants containing derivatives of pyridoxine, pyridoxal or pyridoxamine as effective oxidation dye precursors and as structure-improving additives are unknown to the expert.

It has surprisingly been found in comparative coloring tests that vitamin B6 and certain derivatives have secondary intermediate properties. In particular, it was found that the use of such compounds as secondary intermediate component in hair colorants adds medium golden blond colors to the range of colors. It was also found that the use of the compounds according to the invention during the coloring process leads to an improvement in the structure of hair keratin.

DETAILED DESCRIPTION OF THE INVENTION

In a first embodiment therefore, the present invention relates to a process for coloring keratin fibers, more particularly human hair, in which
  if desired, a pretreatment preparation M1 is applied to the fibers,
  a colorant M2 is then used on the fibers, optionally having been mixed immediately before application to the fibers from:
    a component M2a containing at least one oxidation dye precursor of the primary intermediate type and/or an indole and/or indoline derivative and
    a component M2b containing an oxidizing agent and/or an enzyme, another preparation M3 optionally being added to the individual preparations M2a or M2b before mixing or to the mixture M2 and the colorant M2 being rinsed off the fibers after a contact time of 5 to 30 minutes, characterized in that at least one of the preparations M1, M2a, M2b or M3 contains at least one compound corresponding to formula (I):

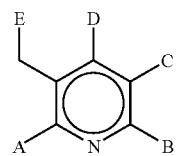

(I)

in which
  A and B independently of one another represent hydrogen, halogen, a $C_{1-4}$ alkyl group, a $C_{3-6}$ cycloalkyl group, a $C_{1-4}$ monohydroxyalkyl group, a $C_{2-4}$ oligohydroxyalkyl group, a $C_{1-4}$ aminoalkyl group, a group —OR or a group —NR$^1$R$^2$, where R$^1$ and R$^2$ independently of one another represent hydrogen, a $C_{1-4}$ alkyl group or a $C_{1-4}$ monohydroxyalkyl group or R$^1$ and R$^2$ together with the nitrogen atom form a saturated ring,
  C represents a group —OR, —NR$^1$R$^2$, —OP(O)(OR$^3$)$_2$, a $C_{1-4}$ monohydroxyalkyl group, a $C_{2-4}$ oligohydroxyalkyl group or a $C_{1-4}$ alkyl group,
  D represents a hydroxy group, a carboxy group, a $C_{1-22}$ alkoxy-carbonyl group, a formyl group, a group —CH$_2$OR or a group —CH$_2$—NR$_2$,
  E represents a group —OR, —OP(O)(OR$^3$)$_2$, a $C_{1-4}$ monohydroxyalkyl group or a $C_{2-4}$ oligohydroxyalkyl group,
  R representing hydrogen, a $C_{1-4}$ alkyl group, a $C_{1-22}$ acyl group, a hydroxy-$C_{2-22}$-acyl group, a $C_{2-10}$ carboxyacyl group, a $C_{3-10}$ oligocarboxyacyl group, an oligocarboxymonohydroxy-$C_{3-10}$-acyl group, an oligocarboxyoligohydroxy-$C_{3-10}$-acyl group, a $C_{3-8}$ cycloalkyl group, a $C_{1-4}$ monohydroxyalkyl group, a $C_{2-4}$ oligohydroxyalkyl group, an aryl group which may contain a hydroxy, nitro or amino group, a heteroaromatic group or a group —CH$_2$CH$_2$NR$^1$R$^2$, where R$^1$ and R$^2$ are as defined above,
  R$^3$ representing hydrogen or a $C_{1-5}$ alkyl group, or one of the corresponding physiologically compatible salts.

Examples of $C_{1-4}$ alkyl groups in the compounds according to the invention are methyl, ethyl, n-propyl, isopropyl, n-butyl and tert.butyl. Preferred alkyl groups are methyl and ethyl. Methyl is a particularly preferred alkyl group. Preferred $C_{3-6}$ cycloalkyl groups are cyclopropyl, cyclobutyl, cyclopentyl, cyclohexyl. Cyclohexyl and cyclopentyl are particularly preferred groups. Preferred $C_{1-4}$ monohydroxyalkyl groups are the groups hydroxymethyl, 2-hydroxyethyl, 3-hydroxypropyl or 4-hydroxybutyl; hydroxymethyl and 2-hydroxyethyl are particularly preferred monohydroxyalkyl groups. A preferred $C_{2-4}$ oligohydroxyalkyl group is the 1,2-dihydroxyethyl group. Preferred $C_{1-22}$ acyl groups are, for example, acetyl, propionyl, butyryl, valeryl, capryl, lauryl, myristyl, palmityl, stearyl, linolyl, behenyl. Examples of a hydroxy-$C_{2-22}$-acyl group are salicylic acid or lactic acid. Preferred $C_{2-10}$ carboxyacyl groups are derived, for example, from malonic acid, succinic acid or adipic acid. One example of a preferred $C_{3-10}$ oligocarboxyacyl group is glyceric acid. A preferred oligocarboxymonohydroxy-$C_{3-10}$-acyl group is derived, for example, from citric acid or malic acid. Preferred oligocarboxyoligohydroxy-$C_{3-10}$-acyl groups are derived, for example, from tartaric acid. According to the invention, preferred halogen substituents are fluorine, chlorine, bromine and iodine; chlorine and bromine are particularly preferred. Physiologically compatible salts in the context of the invention are salts of inorganic or organic acids, for example hydrochlorides, sulfates or hydrobromides. According to the invention, the other terms used are derived from the definitions given here.

The ester derivatives of the compounds corresponding to formula (I) also have physiological and hair-structure-improving properties. This applies in particular to the esters of pyridoxine which can be converted by hydrolysis into pyridoxine. In addition, the ester derivatives acquire improved lipid solubility compared with the non-esterified derivatives. Other examples of carboxylic acid ester derivatives of pyridoxine are derived from the carboxylic acids, such as formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphor acid, benzoic acid, o,m,p-phthalic acid, naphthoic acid, toluylic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrole carboxylic acid, 1,2,4,6,7-naphthalene pentaacetic acid, malonaldehydic acid, 4-hydroxyphthalamidic acid, 1-pyrazole carboxylic acid, gallic acid or propane tricarboxylic acid, and from dicarboxylic acids selected from the group consisting of compounds corresponding to general formula (II):

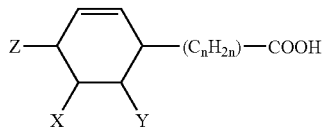

(II)

in which Z represents a linear or branched alkyl or alkenyl group containing 4 to 12 carbon atoms, n is a number of 4 to 12 and one of the two groups X and Y represents a COOH group and the other represents hydrogen or a methyl or ethyl group, dicarboxylic acids corresponding to general formula (II) which additionally contain 1 to 3 methyl or ethyl substituents on the cyclohexene ring and dicarboxylic acids which formally are formed from the dicarboxylic acids (II) by addition of one molecule of water onto the double bond in the cyclohexene ring.

Compounds corresponding to formula (I) in which one of the two groups A and B is hydrogen are preferred.

Compounds corresponding to formula (I) in which one of the two groups A and B is hydrogen and the other group is a $C_{1-4}$ alkyl group are preferred.

Other preferred compounds of formula (I) are those in which C is a hydroxy group, a $C_{1-4}$ monohydroxyalkyl group or a $C_{2-4}$ oligohydroxyalkyl group.

According to the invention, compounds of formula (I) in which D is a hydroxymethyl group, a hydroxy group, a carboxy group or a formyl group are preferred.

Other preferred compounds of formula (I) are those in which E is a hydroxy group or a group —OP(O)(OH)$_2$.

A particularly preferred compound of formula (I) is pyridoxine.

Compounds corresponding to formula (I) such as, for example, pyridoxal, pyridoxal-5-phosphonic acid, pyridoxamine, pyridoxine and 3-hydroxy-5-hydroxymethyl-2-methylpyridine-4-carboxylic acid are commercially obtainable.

In a second embodiment, the present invention relates to a preparation for use in a process for coloring keratin fibers, more particularly human hair, characterized in that it contains at least one compound corresponding to formula (I) or one of the corresponding physiologically compatible salts, preferably in a quantity of 0.1 to 5% by weight, based on the preparation. This preparation acts as the pretreatment preparation M1 in the process according to the invention. A contact time of 1 to 30 minutes is preferred for the preparation M1.

In a third embodiment, the present invention relates to a preparation for coloring keratin fibers, more particularly human hair, which in a first embodiment contains at least one oxidation dye precursor of the primary intermediate type, characterized in that it additionally contains at least one compound corresponding to formula (I) or one of the corresponding physiologically compatible salts. These preparations may optionally contain at least one oxidation dye precursor of the secondary intermediate type.

According to the invention, it can be preferable to use a p-phenylenediamine derivative or a physiologically compatible salt thereof as primary intermediate. Particularly preferred p-phenylenediamine derivatives correspond to formula (E1):

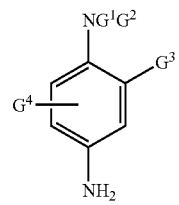

(E1)

in which
G$^1$ stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical, a 4'-aminophenyl radical or a $C_{1-4}$ alkyl radical substituted by a nitrogen-containing group, a phenyl group or a 4'-aminophenyl group;

G$^2$ stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical or a $C_{1-4}$ alkyl radical substituted by a nitrogen-containing group;

G$^3$ stands for a hydrogen atom, a halogen atom, such as a chlorine, bromine, iodine or fluorine atom, a $C_{1-4}$ alkyl radical, a $C_{1-4}$ monohydroxyalkyl radical, a $C_{2-4}$ polyhydroxyalkyl radical, a $C_{1-4}$ hydroxyalkoxy radical, a $C_{1-4}$ acetylaminoalkoxy radical, a $C_{1-4}$ mesylaminoalkoxy radical or a $C_{1-4}$ carbamoylaminoalkoxy radical;

G$^4$ is a hydrogen atom, a halogen atom or a $C_{1-4}$ alkyl radical or if G$^3$ and G$^4$ are in the ortho position to one another, they may together form a bridging α,ω-alkylenedioxo group such as, for example, an ethylenedioxy group.

One example of a preferred $C_{2-4}$ polyhydroxyalkyl group is the α,β-dihydroxyethyl group. Examples of nitrogen-containing groups corresponding to formula (EI) are, in particular, the amino groups, $C_{1-4}$ monoalkylamino groups, $C_{1-4}$ dialkylamino groups, $C_{1-4}$ trialkylammonium groups, $C_{1-4}$ monohydroxyalkylamino groups, imidazolinium and ammonium.

Particularly preferred p-phenylenediamines corresponding to formula (E1) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(β-hydroxyethyl)-p-phenylenediamine, 4-N,N-bis-(β-hydroxyethyl)-amino-2-methylaniline, 4-N,N-bis-(β-hydroxyethyl)-amino-2-chloroaniline, 2-(β-hydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl-β-hydroxyethyl)-p-phenylene-diamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and physiologically compatible salts thereof.

According to the invention, most particularly preferred p-phenylenediamine derivatives corresponding to formula (E1) are p-phenylenediamine, p-toluylenediamine, 2-(β-hydroxyethyl)-p-phenylene-diamine and N,N-bis(β-hydroxyethyl))-p-phenylenediamine.

In another preferred embodiment of the invention, compounds containing at least two aromatic nuclei substituted by amino and/or hydroxyl groups may be used as the primary intermediate.

The binuclear primary intermediates which may be used in the coloring compositions according to the invention include in particular compounds corresponding to formula (E2) and physiologically compatible salts thereof:

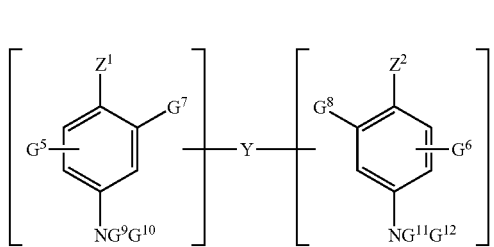

(E2)

in which
  $Z^1$ and $Z^2$ independently of one another stand for a hydroxyl or $NH_2$ radical which is optionally substituted by a $C_{1-4}$ alkyl radical, by a $C_{1-4}$ hydroxyalkyl radical and/or by a bridging group Y or which is optionally part of a bridging ring system,
  the bridging group Y is a $C_{1-14}$ alkylene group such as, for example, a linear or branched alkylene chain or an alkylene ring which may be interrupted or terminated by one or more nitrogen-containing groups and/or one or more hetero atoms, such as oxygen, sulfur or nitrogen atoms, and may optionally be substituted by one or more hydroxyl or $C_{1-8}$ alkoxy radicals or is a direct bond,
  $G^5$ and $G^6$ independently of one another stand for a hydrogen or halogen atom, a $C_{1-4}$ alkyl radical, a $C_{1-4}$ monohydroxyalkyl radical, a $C_{2-4}$ polyhydroxyalkyl radical, a $C_{1-4}$ aminoalkyl radical or a direct bond to the bridging group Y,
  $G^7$, $G^8$, $G^9$, $G^{10}$, $G^{11}$ and $G^{12}$ independently of one another stand for a hydrogen atom, a direct bond to the bridging group Y or a $C_{1-4}$ alkyl radical, with the provisos that
  the compounds of formula (E2) contain only one bridging group Y per molecule and
  the compounds of formula (E2) contain at least one amino group which carries at least one hydrogen atom.

According to the invention, the substituents used in formula (E2) are as defined in the foregoing.

Preferred binuclear primary intermediates corresponding to formula (E2) are, in particular, N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-amino-phenyl)-ethylenediamine, N,N'-bis-(4-aminophenyl)-tetramethylene-diamine, N,N'-bis-(β-hydroxyethyl)-N,N'-bis-(4'-aminophenyl)-tetra-methylenediamine, N,N'-bis-(4-methylaminophenyl)-tetramethylene diamine, N,N'-bis-(ethyl)-N,N'-bis-(4'-amino-3'-methylphenyl)-ethylene-diamine, bis-(2-hydroxy-5-aminophenyl)-methane, 1,4-bis-(4'-amino-phenyl)-diazacycloheptane, N,N'-bis-(2-hydroxy-5-aminobenzyl)-piperazine, N-(4'-aminophenyl)-p-phenylenediamine and 1,10-bis-(2',5'-diaminophenyl)-1,4,7,10-tetraoxadecane and physiologically compatible salts thereof.

Most particularly preferred binuclear primary intermediates corresponding to formula (E2) are N,N'-bis-(β-hydroxyethyl)-N,N'-bis-(4'-aminophenyl)-1,3-diaminopropan-2-ol, bis-(2-hydroxy-5-aminophenyl)-methane, N,N'-bis-(4'-aminophenyl)-1,4-diazacycloheptane and 1,10-bis-(2',5'-diaminophenyl)-1,4,7,10-tetraoxadecane or a physiologically compatible salt thereof.

In another preferred embodiment of the invention, a p-aminophenol derivative or a physiologically compatible salt thereof is used as the primary intermediate. Particularly preferred p-aminophenol derivatives correspond to formula (E3):

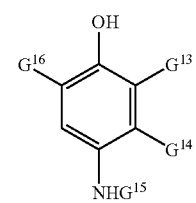

(E3)

in which
  $G^{13}$ stands for a hydrogen atom, a halogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical, a $C_{1-4}$ aminoalkyl radical, a hydroxy-$(C_{1-4})$-alkylamino radical, a $C_{1-4}$ hydroxyalkyoxy radical, a $C_{1-4}$ hydroxyalkyl-$(C_{1-4})$-aminoalkyl radical or a (di-$C_{1-4}$-alkylamino)-$(C_{1-4})$-alkyl radical,
  $G^{14}$ stands for a hydrogen atom or a halogen atom, a $C_{1-4}$ alkyl radical, a $C_{1-4}$ hydroxyalkyl radical, a $C_{2-4}$ polyhydroxyalkyl radical, a $(C_{1-4})$-alkoxy-$(C_{1-4})$-alkyl radical, a $C_{1-4}$ aminoalkyl radical or a $C_{1-4}$ cyanoalkyl radical,
  $G^{15}$ stands for hydrogen, a $C_{1-4}$ alkyl radical, a $C_{1-4}$ hydroxyalkyl radical, a $C_{2-4}$ polyhydroxyalkyl radical, a phenyl radical or a benzyl radical and
  $G^{16}$ stands for hydrogen or a halogen atom.

According to the invention, the substituents used in formula (E3) are defined as in the foregoing.

Preferred p-aminophenols corresponding to formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)-phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)-phenol, 4-amino-2-fluorophenol, 4-amino-2-chlorophenol, 2,6-dichloro-4-aminophenol, 4-amino-2-((diethylamino)-methyl)-phenol and physiologically compatible salts thereof.

Most particularly preferred compounds corresponding to formula (E3) are p-aminophenol, 4-amino-3-methylphenol, 4-amino-2-aminomethylphenol and 4-amino-2-((diethylamino)-methyl)-phenol.

The primary intermediate may also be selected from o-aminophenol and derivatives thereof such as, for example, 2-amino-4-methylphenol or 2-amino-4-chlorophenol.

The primary intermediate may also be selected from heterocyclic primary intermediates such as, for example, the pyridine, pyrimidine, pyrazole, pyrazole/pyrimidine derivatives and physiologically compatible salts thereof. According to the invention, pyrimidine or pyrazole derivatives are preferred.

Preferred pyrimidine derivatives are, in particular, the compounds described in DE 2359399, JP 02019576 A2 and WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triamino-pyrimidine, 2,4-dihydroxy-5,6-diaminopyrimidine and 2,5,6-triaminopyridine.

Preferred pyrazole derivatives are, in particular, the compounds described in DE 3843892, DE 4133957, WO 94/08969, WO 94/08970, EP 740931 and DE 19543988, such as 4,5-diamino-1-methylpyrazole, 4,5-diamino-1-(β-hydroxyethyl)-pyrazole 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl pyrazole, 4,5-diamino-3-tert.butyl-1-methylpyrazole, 4,5-diamino-1-tert.butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)-amino-1-methylpyrazole.

Preferred pyridine derivatives are, in particular, the compounds described in GB 1,026,978 and GB 1,153,196, such as 2,5-diaminopridine, 2-(4-methoxyphenyl)-amino-3-aminopyridine, 2,3-diamino-6-methoxypyridine, 2-(β-methoxyethyl)-amino-3-amino-6-methoxypyridine and 3,4-diaminopyridine.

Preferred pyrazole-pyrimidine derivatives are, in particular, the derivatives of pyrazole-[1,5-a]-pyrimidine corresponding to formula (E4) below and tautomeric forms thereof where a tautomeric equilibrium exists:

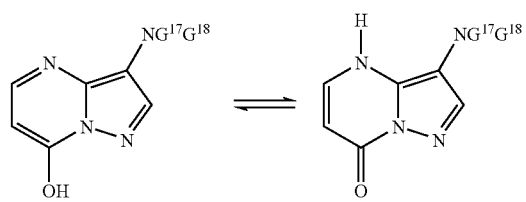

(E4)

in which
G$^{17}$, G$^{18}$, G$^{19}$ and G$^{20}$ independently of one another stand for a hydrogen atom, a C$_{1-4}$ alkyl radical, an aryl radical, a C$_{1-4}$ hydroxyalkyl radical, a C$_{2-4}$ polyhydroxyalkyl radical, a (C$_{1-4}$)-alkoxy-(C$_{1-4}$)-alkyl radical, a C$_{1-4}$ aminoalkyl radical which may optionally be protected by an acetylureide or sulfonyl radical, a (C$_{1-4}$)-alkylamino-(C$_{1-4}$)-alkyl radical, a di[(C$_{1-4}$)-alkyl]-(C$_{1-4}$)-aminoalkyl radical, the dialkyl radicals optionally forming a carbon cycle or a heterocycle with 5 or 6 links, a C$_{1-4}$ hydroxyalkyl or a di-(C$_{1-4}$)-[hydroxyalkyl]-(C$_{1-4}$)-aminoalkyl radical;
the X radicals independently of one another stand for a hydrogen atom, a C$_{1-4}$ alkyl radical, an aryl radical, a C$_{1-4}$ hydroxyalkyl radical, a C$_{2-4}$ polyhydroxyalkyl radical, a C$_{1-4}$ aminoalkyl radical, a (C$_{1-4}$)-alkylamino-(C$_{1-4}$)-alkyl radical, a di[(C$_{1-4}$)-alkyl]-(C$_{1-4}$)-aminoalkyl radical, the dialkyl radicals optionally forming a carbon cycle or a heterocycle with 5 or 6 links, a C$_{1-4}$ hydroxyalkyl or a di-(C$_{1-4}$)-[hydroxyalkyl]-(C$_{1-4}$)-aminoalkyl radical, an amino radical, a C$_{1-4}$ alkyl or a di-(C$_{1-4}$ hydroxyalkyl)-amino radical, a halogen atom, a carboxylic acid group or a sulfonic acid group,
i has the value 0, 1, 2 or 3,
p has the value 0 or 1,
q has the value 0 or 1 and
n has the value 0 or 1, with the proviso that
the sum of p+q is not 0,
where p+q=2, n has the value 0 and the groups NG$^{17}$G$^{18}$ and NG$^{19}$G$^{20}$ occupy the (2,3); (5,6); (6,7); (3,5) or (3,7) positions;
where p+q=1, n has the value 1 and the groups NG$^{17}$G$^{18}$ (or NG$^{19}$G$^{20}$) and the group OH occupy the (2,3); (5,6); (6,7); (3,5) or (3,7) positions.

The substituents used in formula (E4) are as defined in the foregoing.

If the pyrazole-[1,5-a]-pyrimidine corresponding to formula (E4) above contains a hydroxy group in one of the positions 2, 5 or 7 of the ring system, a tautomeric equilibrium exists as illustrated, for example, in the following scheme:

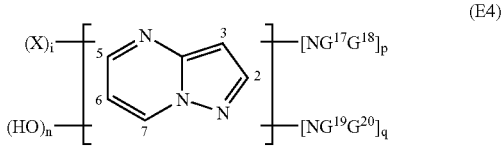

Among the pyrazole-[1,5-a]-pyrimidines corresponding to formula (V) above, the following may be particularly mentioned:
pyrazole-[1,5-a]-pyrimidine-3,7-diamine;
2,5-dimethylpyrazole-[1,5-a]-pyrimidine-3,7-diamine;
pyrazole-[1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino)-ethanol;
2-(7-aminopyrazole-[1,5-a]-pyrimidin-3-ylamino)-ethanol;
2-[(3-aminopyrazole-[1,5-a]-pyrimidin-7-yl)-(2-hydroxyethyl)-amino]-ethanol;
2-[(7-aminopyrazole-[1,5-a]-pyrimidin-3-yl)-(2-hydroxyethyl)-amino]-ethanol;
5,6-dimethylpyrazole-[1,5-a]-pyrimidine-3,7-diamine;
2,6-dimethylpyrazole-[1,5-a]-pyrimidine-3,7-diamine;
2,5,N7,N7-tetramethylpyrazole-[1,5-a]-pyrimidine-3,7-diamine;

and physiologically compatible salts thereof and tautomeric forms thereof where a tautomeric equilibrium exists.

The pyrazole-[1,5-a]-pyrimidines corresponding to formula (V) above may be prepared by cyclization from an aminopyrazole or from hydrazine, as described in the literature.

According to the invention, preferred primary intermediates are derivatives of p-phenylenediamine, derivatives of pyrimidine, derivatives of pyrazole and of p-aminophenol.

According to the invention, particularly preferred primary intermediates are p-phenylenediamine, p-toluylenediamine, 2-(β-hydroxyethyl)-p-phenylenediamine, N,N-bis-(β-hydroxyethyl)-p-phenylenediamine, 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine, 2,5,6-triaminopyrimidine, 4,5-diamino-1-methylpyrazole, 4,5-diamino-1-(β-hydroxyethyl)-pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.butyl-1-methylpyrazole, 4,5-diamino-1-tert.butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl pyrazole, 4,5-diamino-3-methyl-1-isopropyl pyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)-amino-1-methylpyrazole, p-aminophenol, 4-amino-3-methylphenol, 4-amino-3-fluorophenol, 4-amino-2-aminomethylphenol and 4-amino-2-((diethylamino)-methyl)-phenol.

According to the invention, most particularly preferred primary intermediates are p-phenylenediamine, p-toluylenediamine, 2-(β-hydroxyethyl)-p-phenylenediamine and N,N-bis-(β-hydroxyethyl)-p-phenylenediamine, 2,4,5,6-tetraaminopyrimidine, 4,5-diamino-1-(β-hydroxyethyl)-pyrazole, 4-amino-3-methylphenol and 4-amino-2-aminomethylphenol.

According to invention, the secondary intermediates used are, in particular, m-phenylenediamine derivatives, naphthols, resorcinol and resorcinol derivatives, pyrazolones and m-aminophenols.

According to the invention, preferred secondary intermediates are:

m-aminophenol and derivatives thereof such as, for example, 5-amino-2-methylphenol, N-cyclopentyl-3-aminopenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-(ethylamino)-4-methylphenol and 2,4-dichloro-3-aminophenol, o-aminophenol and derivatives thereof, m-diaminobenzene and derivatives thereof such as, for example, 2,4-diaminophenoxyethanol, 1,3-bis-(2',4'-diaminophenoxy)-propane, 1-methoxy-2-amino-4-(2'-hydroxyethylamino)-benzene, 1,3-bis-(2',4'-diaminophenyl)-propane, 2,6-bis-(2'-hydroxyethylamino)-1-methylbenzene and 1-amino-3-bis-(2'-hydroxyethyl)-aminobenzene, o-diaminobenzene and derivatives thereof such as, for example, 3,4-diaminobenzoic acid and 2,3-diamino-1-methylbenzene, di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene, pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diamino-pyridine, 2,3-diamino-6-methoxypyridine and 3,5-diamino-2,6-dimethoxypyridine, naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihroxy-naphthalene, 1,8-dihydroxynaphthalene, 2,7-dihdroxynaphthalene and 2,3-dihdroxynaphthalene, morpholine derivatives such as, for example, 6-hydroxybenzomorpholine and 6-aminobenzomorpholine, quinoxaline derivatives such as, for example, 6-methyl-1,2,3,4-tetrahydroquinoxaline, pyrazole derivatives such as, for example, 1-phenyl-3-methylpyrazol-5-one, indole derivatives such as, for example, 4-hydroxyindole, 6-hydroxyindole and 7-hydroxyindole, pyrimidine derivatives such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or methylenedioxybenzene derivatives such as, for example, 1-hydroxy-3,4-methylenedioxybenzene, 1-amino-3,4-methylene-dioxybenzene and 1-(2'-hydroxyethyl)-amino-3,4-methylene-dioxybenzene.

Particularly preferred secondary intermediates are, for example, 2-amino-3-hydroxypyridine, 2-amino-3-hydroxy-5-chloropyridine, 3-amino-2-methylamino-6-methoxypyridine, 3,5-diamino-2,6-dimethoxypyridine, 2,6-dihydroxy-3,4-dimethylpyridine, m-phenylenediamine, 2,6-bis-(2-hydroxyethylamino)-toluene, 3-amino-2,4-dichlorophenol, 3-amino-2-chloro-6-methylphenol, 5-amino-4-chloro-2-methylphenol, 5-(β-hydroxyethyl)-amino-2-methylphenol, 5-amino-2-methylphenol, 2-methylresorcinol, 2-(2',4'-diaminophenoxy)-ethanol, 1,3-bis-(2',4'-diaminophenoxy)-propane, resorcinol, 4-chlororesorcinol, resorcinol monomethylether, m-aminophenol, 1,7-, 2,7- and 1,5-dihydroxynaphthalene and 4-hydroxyindole and 6-hydroxyindole.

The hair colorants according to the invention contain both the primary intermediates and the secondary intermediates in a quantity of preferably 0.005 to 10% by weight and more preferably in a quantity of 0.1 to 5% by weight, based on the oxidation colorant as a whole.

The primary intermediates and secondary intermediates are generally used in a substantially equimolar ratio to one another. Although it has proved to be of advantage to use the primary and secondary intermediates in an equimolar ratio, there is no disadvantage in using individual oxidation dye precursors in a certain excess so that primary intermediates and secondary intermediates may be present in a molar ratio of 1:0.5 to 1:3 and, more particularly, 1:1 to 1:2.

A second embodiment is a preparation for coloring keratin fibers, more particularly human hair, which contains at least one indole and/or indoline derivative, characterized in that it contains a compound corresponding to formula (I) or one of the corresponding physiologically compatible salts.

Indoles and/or indolines containing at least one hydroxy or amino group, preferably as a substituent on the six ring, are used as precursors of "nature-analogous" dyes in the preparations according to the invention of the second embodiment. These groups may carry further substituents, for example in the form of an etherification or esterification of the hydroxy group or an alkylation of the amino group.

Particularly suitable precursors of "nature-analogous" hair dyes are derivatives of 5,6-dihydroxyindoline corresponding to formula (IIIa):

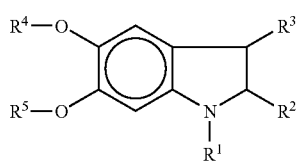

(IIIa)

in which—independently of one another—
$R^1$ is hydrogen, a $C_{1-4}$ alkyl group, a $C_{3-6}$ cycloalkyl group, a $C_{2-4}$ alkenyl group or a $C_{1-4}$ hydroxyalkyl group,
$R^2$ is hydrogen or a —COOH group, the —COOH group optionally being present as a salt with a physiologically compatible cation,
$R^3$ is hydrogen or a $C_{1-4}$ alkyl group,
$R^4$ is hydrogen, a $C_{1-4}$ alkyl group or a group —CO—$R^6$, where $R^6$ is a $C_{1-4}$ alkyl group, and
$R^5$ is one of the groups mentioned for $R^4$, and physiologically compatible salts of these compounds with an organic or inorganic acid.

Particularly preferred derivatives of indoline are 5,6-dihydroxy-indoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxy-indoline-2-carboxylic acid and 6-hydroxyindoline, 6-aminoindoline and 4-aminoindoline.

Within this group, particular emphasis is placed on N-methyl-5,6-dihydroxyindoline, N-ethyl-5,6-dihydroxyindoline, N-propyl-5,6-dihydroxy-indoline, N-butyl-5,6-dihydroxyindoline and, in particular, 5,6-dihydroxy-indoline.

Other particularly suitable precursors of "nature-analogous" hair dyes are derivatives of 5,6-dihydroxyindole corresponding to formula (IIIb):

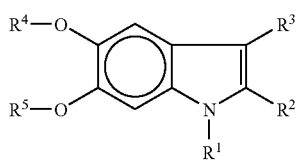

(IIIb)

in which—independently of one another—
$R^1$ is hydrogen, a $C_{1-4}$ alkyl group, a $C_{3-6}$ cycloalkyl group, a $C_{2-4}$ alkenyl group or a $C_{1-4}$ hydroxyalkyl group,
$R^2$ is hydrogen or a —COOH group, the —COOH group optionally being present as a salt with a physiologically compatible cation,
$R^3$ is hydrogen or a $C_{1-4}$ alkyl group,
$R^4$ is hydrogen, a $C_{1-4}$ alkyl group or a group —CO—$R^6$, where $R^6$ is a $C_{1-4}$ alkyl group, and
$R^5$ is one of the groups mentioned for $R^4$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives may be used both as free bases and in the form of their physiologically compatible salts with inorganic or organic acids, for example hydrochlorides, sulfates and hydrobromides, in the colorants according to the invention. The indole or indoline derivatives are present in these colorants in quantities of normally 0.05 to 10% by weight and preferably 0.2 to 5% by weight.

Where dye precursors of the indoline or indole type in particular are used, it can be of advantage to use an amino acid and/or an oligopeptide as alkalizing agent.

At least one oxidation dye precursor of the primary intermediate type may also be present as an optional constituent. The preferred primary intermediates and the quantities used correspond to those of the first embodiment.

In a third embodiment, the hair colorants of the first and second embodiments according to the invention additionally contain typical substantive dyes besides the oxidation dye precursors for further modifying the shades. Substantive dyes are typically nitrophenylenediamines, nitroaminophenols, azo dyes, anthraquinones or indophenols. Preferred substantive dyes are the compounds known under the International names or commercial names of HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 12, Disperse Blue 3, HC Violet 1, Disperse Violet 1, Disperse Violet 4, Acid Violet 43, Disperse Black 9 and Acid Black 52 and also 1,4-diamino-2-nitrobenzene, 2-amino-4-nitrophenol, 1,4-bis-(β-hydroxyethyl)-amino-2-nitrobenzene, 3-nitro-4-(β-hydroxyethyl)-aminophenol, 2-(2'-hydroxyethyl)-amino-4,6-dinitrophenol, 1-(2'-hydroxyethyl)-amino-4-methyl-2-nitro-benzene, 1-amino-4-(2'-hydroxyethyl)-amino-5-chloro-2-nitrobenzene, 4-amino-3-nitrophenol, 1-(2'-ureidoethyl)-amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

According to the invention, cationic substantive dyes may also be used as substantive dyes. Particularly preferred are
(a) cationic triphenylmethane dyes such as, for example, Basic Blue 7, Basic Blue 26, Basic Violet 2 and Basic Violet 14,
(b) aromatic systems substituted by a quaternary nitrogen group such as, for example, Basic Yellow 57, Basic Red 76, Basic Blue 99, Basic Brown 16 and Basic Brown 17 and
(c) substantive dyes containing a heterocycle with at least one quaternary nitrogen atom as disclosed, for example, in EP-A2 998 908, to which reference is specifically made at this juncture, in claims 6 to 11.

Preferred cationic substantive dyes of group (c) are, in particular, the following compounds:

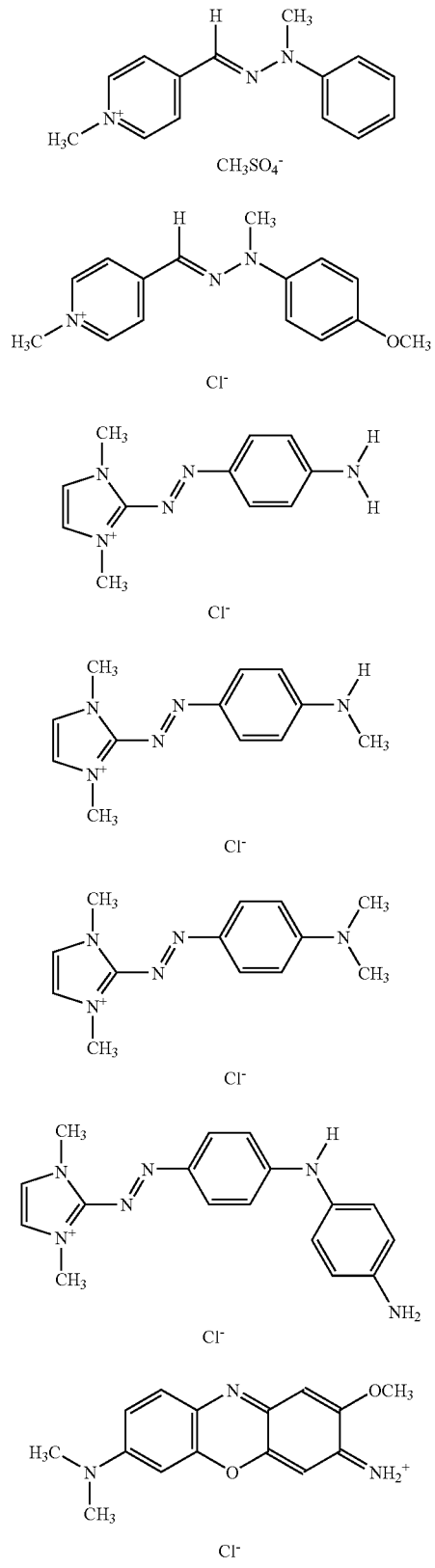

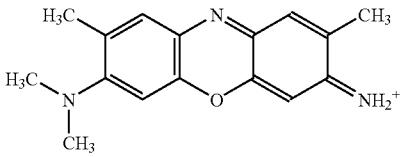

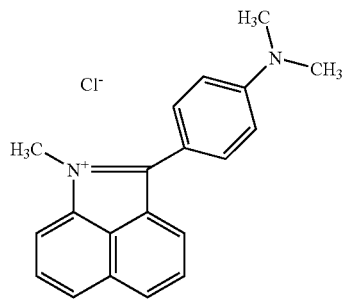

The compounds corresponding to formula (DZ1), (DZ3) and (DZ5) are most particularly preferred cationic substantive dyes of group (c). According to the invention, the cationic substantive dyes marketed under the name of Arianor® are particularly preferred substantive dyes.

The preparations according to the invention of this embodiment preferably contain the substantive dyes in a quantity of 0.01 to 20% by weight, based on the colorant as a whole.

All the colorants according to the invention contain the compounds of formula (I) according to the invention in a quantity of preferably 0.05 to 5% by weight and more particularly 0.1 to 1% by weight, based on the colorant as a whole.

The preparations according to the invention may also contain naturally occurring dyes such as, for example, henna red, henna neutral, henna black, camomile blossom, sandalwood, black tea, black alder bark, sage, logwood, madder root, catechu, sedre and alkanet.

The preparations according to the invention contain dye precursors preferably in a suitable aqueous, alcoholic or aqueous/alcoholic carrier. For coloring hair, such carriers are, for example, creams, emulsions, gels or even surfactant-containing foaming solutions such as, for example, shampoos, foam aerosols or other preparations suitable for application to the hair. However, the dye precursors may even be integrated into a powder-form or tablet-form formulation.

Aqueous/alcoholic solutions in the context of the invention are aqueous solutions containing 3 to 70% by weight of a $C_{1-4}$ alcohol, more particularly ethanol or isopropanol. The preparations according to the invention may additionally contain other organic solvents such as, for example, methoxybutanol, benzyl alcohol, ethyl diglycol or 1,2-propylene glycol. Water-soluble organic solvents are preferred.

In principle, the color can be oxidatively developed with atmospheric oxygen. However, a chemical oxidizing agent is preferably used, particularly when human hair is to be not only colored, but also lightened. Particularly suitable oxidizing agents are persulfates, chlorites and, in particular, hydrogen peroxide or addition products thereof with urea, melamine or sodium borate. Oxidation may also be carried out with enzymes. In this case, the enzymes may be used both to produce oxidizing per compounds and to enhance the effect of an oxidizing agent present in small quantities. Thus, the enzymes (enzyme class 1: oxidoreductases) can transfer electrons from suitable primary intermediates (reducing agents) to atmospheric oxygen. Oxidases, such as tyrosinase, ascorbate oxidase and laccase, are preferred for this purpose, as are glucoseoxidase, uricase or pyruvate oxidase. Mention is also made of the procedure whereby the effect of small quantities (for example 1% and less, based on the formulation as a whole) of hydrogen peroxide is enhanced by peroxidases.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps),
ether carboxylic acids corresponding to the formula R—O—($CH_2$—$CH_2$O)$_x$—$CH_2$—COOH, in which R is a linear alkyl group containing 10 to 22 carbon atoms and x=0 or 1 to 16,
acyl sarcosides containing 10 to 18 carbon atoms in the acyl group,
acyl taurides containing 10 to 18 carbon atoms in the acyl group,
acyl isethionates containing 10 to 18 carbon atoms in the acyl group,
sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups,
linear alkane sulfonates containing 12 to 18 carbon atoms,
linear α-olefin sulfonates containing 12 to 18 carbon atoms,
α-sulfofatty acid methyl esters of fatty acids containing 12 to 18 carbon atoms,
alkyl sulfates and alkyl polyglycol ether sulfates corresponding to the formula R—O($CH_2$—$CH_2$O)$_x$—$SO_3$H, in which R is a preferably linear alkyl group containing 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids containing 12 to 24 carbon atoms and 1 to 6 double bonds according to DE-A-39 26 344,
esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

Nonionic surfactants contain, for example, a polyol group, a poly-alkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group,
$C_{12-22}$ fatty acid monoesters and diesters of products of the addition of 1 to 30 moles of ethylene oxide onto glycerol,
$C_{8-22}$ alkyl mono- and oligoglycosides and ethoxylated analogs thereof and
products of the addition of 5 to 60 moles of ethylene oxide onto castor oil and hydrogenated castor oil.

Preferred nonionic surfactants are alkyl polyglycosides corresponding to the general formula $R^1O$—$(Z)_x$. These compounds are characterized by the following parameters.

The alkyl group $R^1$ contains 6 to 22 carbon atoms and may be both linear and branched. Primary linear and 2-methyl-branched aliphatic groups are preferred. Such alkyl groups are, for example, 1-octyl, 1-decyl, 1-lauryl, 1-myristyl, 1-cetyl and 1-stearyl. 1-Octyl, 1-decyl, 1-lauryl and 1-myristyl are particularly preferred. Where so-called "oxo alcohols" are used as starting materials, compounds with an odd number of carbon atoms in the alkyl chain predominate.

The alkyl polyglyosides suitable for use in accordance with the invention may, for example, contain only one particular alkyl group $R^1$. However, such compounds are normally prepared from natural fats and oils or mineral oils. In this case, mixtures corresponding to the starting compounds or corresponding to the particular working up of these compounds are present as the alkyl groups R.

Particularly preferred alkyl polyglycosides are those in which $R^1$ consists
essentially of $C_8$ and $C_{10}$ alkyl groups,
essentially of $C_{12}$ and $C_{14}$ alkyl groups,
essentially of $C_8$ to $C_{16}$ alkyl groups or
essentially of $C_{12}$ to $C_{16}$ alkyl groups.

Any mono- or oligosaccharides may be used as the sugar unit Z. Sugars containing 5 or 6 carbon atoms and the corresponding oligosaccharides are normally used. Examples of such sugars are glucose, fructose, galactose, arabinose, ribose, xylose, lyxose, allose, altrose, mannose, gulose, idose, talose and sucrose. Preferred sugar units are glucose, fructose, galactose, arabinose and sucrose; glucose is particularly preferred.

The alkyl polyglycosides suitable for use in accordance with the invention contain on average 1.1 to 5 sugar units. Alkyl polyglycosides with x values of 1.1 to 1.6 are preferred. Alkyl glycosides where x is 1.1 to 1.4 are most particularly preferred.

Besides acting as surfactants, the alkyl glycosides may also be used to improve the fixing of perfume components to the hair. Accordingly, in cases where the effect of the perfume oil on the hair is intended to last longer than the duration of the hair treatment, alkyl glycosides will preferably be used as another ingredient of the preparations according to the invention.

Alkoxylated homologs of the alkyl polyglycosides mentioned may also be used in accordance with the invention. These homologs may contain on average up to 10 ethylene oxide and/or propylene oxide units per alkyl glycoside unit.

Zwitterionic surfactants may also be used, particularly as co-surfactants. In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Also suitable, particularly as co-surfactants, are ampholytic surfactants. Ampholytic surfactants are surface-active compounds which, in addition to a C$_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and C$_{12-18}$ acyl sarcosine.

According to the invention, the cationic surfactants used are particularly those of the quaternary ammonium compound, esterquat and amidoamine type.

Preferred quaternary ammonium compounds are ammonium halides, more particularly chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride and the imidazolium compounds known under the INCI names of Quaternium-27 and Quaternium-83. The long alkyl chains of the above-mentioned surfactants preferably contain 10 to 18 carbon atoms.

Esterquats are known substances which contain both at least one ester function and at least one quaternary ammonium group as structural element. Preferred esterquats are quaternized ester salts of fatty acids with triethanolamine, quaternized ester salts of fatty acids with diethanol alkylamines and quaternized ester salts of fatty acids with 1,2-dihydroxypropyl dialkylamines. Such products are marketed, for example, under the names of Stepantex®, Dehyquart® and Armocare®. The products Armocare® VGH-70, an N,N-bis-(2-palmitoyloxyethyl)-dimethyl ammonium chloride, and Dehyquart® F-75 and Dehyquart® AU-35 are examples of such esterquats.

The alkyl amidoamines are normally prepared by amidation of natural or synthetic fatty acids and fatty acid cuts with dialkyl aminoamines. A compound from this group particularly suitable for the purposes of the invention is the stearamidopropyl dimethylamine obtainable under the name of Tegoamid® S 18.

Other cationic surfactants suitable for use in accordance with the invention are the quaternized protein hydrolyzates.

Also suitable for the purposes of the invention are cationic silicone oils such as, for example, the commercially available products Q2-7224 (manufacturer: Dow Corning; a stabilized trimethyl silyl amodimethicone), Dow Corning 929 Emulsion (containing a hydroxyamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

One example of a quaternary sugar derivative suitable for use as a cationic surfactant is the commercially available product Glucquat®100 (INCI name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

The preparations according to the invention preferably may also contain a conditioning agent selected from the group consisting of cationic surfactants, cationic polymers, alkyl amidoamines, paraffin oils, vegetable oils and synthetic oils.

Cationic polymers can be preferred conditioning agents. These are generally polymers containing a quaternary nitrogen atom, for example in the form of an ammonium group. The following are examples of preferred cationic polymers:

Quaternized cellulose derivatives commercially available under the names of Celquat® and Polymer JR®. The compounds Celquat® H 100, Celquat® L 200 and Polymer JR®400 are preferred quaternized cellulose derivatives.

Polymeric dimethyl diallyl ammonium salts and copolymers thereof with acrylic acid and with esters and amides of acrylic acid and methacrylic acid. The products commercially available under the names of Merquat®100 (poly(dimethyl diallyl ammonium chloride)), Merquat®550 (dimethyl diallyl ammonium chloride/acrylamide copolymer) and Merquat® 280 (dimethyl diallyl ammonium chloride/acrylic acid copolymer) are examples of such cationic polymers.

Copolymers of vinyl pyrrolidone with quaternized derivatives of dialkylaminoacrylate and methacrylate, such as vinyl pyrrolidone/dimethylaminomethacrylate copolymers quaternized, for example, with diethyl sulfate.

Compounds such as these are commercially available under the names of Gafquat®734 and Gafquat®755.

Copolymers of vinyl pyrrolidone with methoimidazolinium chloride which are commercially available under the name of Luviquat®.

Quaternized polyvinyl alcohol.

The polymers with quaternary nitrogen atoms in the main polymer chain known by the names of Polyquaternium 2, Polyquaternium 17, Polyquaternium18 and Polyquaternium 27.

Cationic polymers from the first four groups mentioned are particularly preferred, Polyquaternium 2, Polyquaternium 10 and Polyquaternium 22 being most particularly preferred.

In a particularly preferred embodiment, zwitterionic or ampholytic polymers are used alternatively to the cationic polymers as conditioning agents. Preferred representatives are octylacrylamide/methyl methacrylate/tert.butyl aminoethyl methacrylate/2-hydroxypropyl methacrylate copolymers and in particular the acrylamidopropyl trimethyl ammonium chloride/acrylate copolymer.

Other suitable conditioning agents are silicone oils, more particularly dialkyl and alkylaryl siloxanes, such as for example dimethyl polysiloxane and methylphenyl polysiloxane, and alkoxylated and quaternized analogs thereof. Examples of such silicones are the products marketed by Dow Corning under the names of DC 190, DC 200, DC 344, DC 345 and DC 1401 and the products Q2-7224 (manufacturer: Dow Corning; a stabilized trimethyl silyl amodimethicone), Dow Corning® 929 Emulsion (containing a hydroxylamino-modified silicone which is also known as amodimethicone), SM-2059 (manufacturer: General Electric), SLM-55067 (manufacturer: Wacker) and Abil® Quat 3270 and 3272 (manufacturer: Th. Goldschmidt; diquaternary polydimethyl siloxanes, Quaternium-80).

Other suitable conditioning agents are paraffin oils, synthetically produced oligomeric alkenes and vegetable oils, such as jojoba oil, sunflower oil, orange oil, almond oil, wheatgerm oil and peach kernel oil.

Phospholipids, for example soya lecithin, egg lecithin and kephalins, are also suitable hair-conditioning compounds.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as maleic acid and lactic acid, hair-conditioning compounds, such as phospholipids, for example soya lecithin, egg lecithin and kephalins, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solvents and solubilizers, such as ethanol, isopropanol, ethylene glycol, propylene glycol, glycerol and diethylene glycol, fiber-structure-improving agents, more particularly mono-, di- and oligosaccharides such as, for example, glucose, galactose, fructose and lactose, quaternized amines, such as methyl-1-alkylamidoethyl-2-alkylimidazolinium methosulfate, defoamers, such as silicones, dyes for coloring the preparation, antidandruff agents, such as piroctone olamine, zinc omadine and climbazol, UV filters, more particularly derivatized benzophenones, cinnamic acid derivatives and triazines, substances for adjusting the pH value, for example typical acids, more particularly food-grade acids and bases, active substances, such as allantoin, pyrrolidone carboxylic acids and salts thereof and bisabolol, vitamins, provitamins and vitamin precursors, more particularly those of groups A, $B_3$, $B_5$, C, E, F and H, plant extracts, such as the extracts of green tea, oak bark, stinging nettle, hamamelis, hops, camomile, burdock root, horse willow, hawthorn, lime blossom, almond, aloe vera, pine needle, horse chestnut, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root, cholesterol, consistency factors, such as sugar esters, polyol esters or polyol alkyl ethers, fats and waxes, such as spermaceti, beeswax, montan wax and paraffins, fatty acid alkanolamides, complexing agents, such as EDTA, NTA, β-alanine diacetic acid and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, styrene/PVP and styrene/acrylamide copolymers, pearlizers, such as ethylene glycol mono- and distearate and PEG-3-distearate, pigments, stabilizers for hydrogen peroxide and other oxidizing agents, propellents, such as propane/butane mixtures, $N_2O$, dimethyl ether, $CO_2$ and air, antioxidants.

Information on other optional components and the quantities in which they are used can be found in the reference books known to the expert, for example Kh. Schrader, Grundlagen und Rezepturen der Kosmetika, 2nd Edition, Hüthig Buch Verlag, Heidelberg, 1989.

In a third embodiment, the present invention relates to a kit for use in a process for coloring keratin fibers, more particularly human hair. The first embodiment is characterized in that the kit consists of the following separately packed components:

a pretreatment preparation M1 according to claim 8 or 18, a coloring component M2a containing at least one oxidation dye precursor of the primary intermediate type and/or an indole and/or indoline derivative and optionally at least one oxidation dye precursor of the secondary intermediate type.

In a preferred embodiment, this kit additionally contains a separately packed preparation M2b containing an oxidizing agent and/or enzyme.

A second embodiment of the kit is characterized in that it consists of the following separately packed components:

- a coloring component M2a containing at least one oxidation dye precursor of the primary intermediate type and/or an indole or indoline derivative and optionally at least one oxidation dye precursor of the secondary intermediate type and/or a substantive dye,
- a preparation M3 containing at least one compound corresponding to formula (I) or one of the corresponding physiologically compatible salts.

In a preferred embodiment, this kit additionally contains a separately packed preparation M2b containing an oxidizing agent and/or an enzyme, If an enzyme is used, optionally together with an oxidizing agent, in the preparation M2b, M2b is preferably made up in solid form as a powder in accordance with the invention.

In a fourth embodiment, the present invention relates to the use of the kit according to the invention in a process for coloring keratin fibers, more particularly human hair.

The following Examples are intended to illustrate the invention.

EXAMPLES

1. Coloring Examples

A) Comparison Colorings

A1) Preparation of the Coloring Creams

To produce the reference coloring cream or the comparison coloring cream, an emulsion (mixture A) and a mixture B were always prepared. The reference coloring cream contains only one primary intermediate. For preparing the comparison coloring cream, this primary intermediate was combined with a compound corresponding to formula (I) in a quantity ratio of 1:1 (Table 1, Example 1.A.1–1.A.5). In a control experiment, only the compound of formula (I) was used (Table 1, Example 1.A.6).

| Mixture A | |
|---|---|
| Hydrenol ® D[1] | 8.50 g |
| Kokoslorol ® C12–18[2] | 2.00 g |
| Eumulgin ® B2[3] | 0.75 g |
| Texapon ® NSO[4] | 20.00 g |
| Dehyton ® K[5] | 12.50 g |
| Water | 30.00 g |

[1]$C_{16-18}$ fatty alcohol (INCI name: Cetearyl Alcohol) (COGNIS)
[2]$C_{12-18}$ fatty alcohol (INCI name: Coconut Alcohol) (COGNIS)
[3]cetylstearyl alcohol with ca. 20 EO units (INCI name: Ceteareth-20) (COGNIS)
[4]lauryl ether sulfate, sodium salt (ca. 27.5% active substance: INCI name: Sodium Laureth Sulfate) (COGNIS)
[5]N,N-dimethyl-N-($C_{8-18}$ cocoamidopropyl)-ammonium acetobetaine (ca. 30% active substance; INCI name: Aqua (Water), Cocamidopropyl Betaine) (COGNIS)

The substances Hydrenol® D, Kokoslorol®C12–18, Eumulgin® B2, Texapon® NSO and Dehyton® K were melted at 80° C., mixed with the water (heated to 80° C.) and emulsified with vigorous stirring. The emulsion was then cooled with gentle stirring.

| Mixture B | |
|---|---|
| Sodium sulfite | 1.00 g |
| Ammonium sulfate | 1.00 g |
| Dye precursors | as shown in Table 1 |
| Ammonia (25% solution) | to pH 10 |
| Water | 10.00 g |

The dye precursors were dissolved in the water (heated to 50° C.) while the sodium sulfite and ammonium sulfate were added. The pH was adjusted to 10 with ammonia.

Mixture B was added with stirring to mixture A and the coloring cream obtained was made up with water to 100 g and cooled to room temperature.

A2) Coloring of the Fibers 50 ml of the coloring cream obtained in accordance with A1) was mixed with a 3% $H_2O_2$ solution and the mixture was applied to 5 cm long tresses of "Euronaturhaar blond" (Kerling). After a contact time of 30 minutes at 32°, the hair was rinsed, washed with a standard shampoo and then dried.

The results are set out in Table 1. The CIELAB co-ordinates shown are a measure of L (lightness), a (color red-green component), b (color yellow-blue component), C (brightness) and h (tone) and are calculated from the standard color values X, Y and Z which are in turn derived from the spectral distributions of the degree of reflection of the sample (H. G. Völz, Industrielle Farbprüfung, VCH, Weinheim, 1990).

TABLE 1

| Example | Primary intermediate quantity [mmol] | Pyridoxine.HCI quantity [mmol] | Shade obtained | L | a | b | C | h |
|---|---|---|---|---|---|---|---|---|
| 1.A.1 | E1/7.5 | | Dark brown | 38 | 9 | 18 | 20 | 64 |
| 1.A.2 | E1/15.0 | | Mustard brown | 29 | 9 | 13 | 16 | 56 |
| 1.A.3 | E1/7.5 | 7.5 | Yellow-brown | 41 | 10 | 25 | 27 | 68 |
| 1.A.4 | E2/3.0 | | Brown | 37 | 7 | 14 | 16 | 62 |
| 1.A.5 | E2/3.0 | 3.0 | Yellow-brown | 43 | 12 | 26 | 28 | 65 |
| 1.A.6 | | 15.0 | Pale yellow | 67 | 4 | 25 | 25 | 81 |

E1 4-amino-2-aminomethyl phenol.2 HCl
E2 p-toluylenediamine.H$_2$SO$_4$

B) Coloring Examples with Pyridoxine in Combination with Several Secondary and Primary Intermediates B1) Preparation of the Coloring Creams To produce coloring creams 1 and 2, an emulsion (mixture A) and the mixtures B for coloring cream 1 and C for coloring cream 2 were prepared.

| Mixture A: | |
|---|---|
| Hydrenol ® D[1] | 8.50 g |
| Kokoslorol ® C12–18[2] | 2.00 g |
| Eumulgin ® B2[3] | 0.75 g |
| Texapon ® NSO[4] | 15.00 g |
| Dehyton ® K[5] | 12.50 g |
| Water | 30.00 g |

[1]C$_{16-18}$ fatty alcohol (INCI name: Cetearyl Alcohol) (COGNIS)
[2]C$_{12-18}$ fatty alcohol (INCI name: Coconut Alcohol) (COGNIS)
[3]cetylstearyl alcohol with ca. 20 EO units (INCI name: Ceteareth-20) (COGNIS)
[4]lauryl ether sulfate, sodium salt (ca. 27.5% active substance: INCI name: Sodium Laureth Sulfate) (COGNIS)
[5]N,N-dimethyl-N-(C$_{8-18}$ cocoamidopropyl)-ammonium acetobetaine (ca. 30% active substance; INCI name: Aqua (Water), Cocamidopropyl Betaine) (COGNIS)

The substances Hydrenol® D, Kokoslorol® C12–18 and Eumulgin® B2 were melted at 80° C., mixed with the water (heated to 80° C.) containing the Texapon® NSO and Dehyton® K and emulsified with vigorous stirring. The emulsion was then cooled with gentle stirring.

| Mixture B (for coloring cream 1) | |
|---|---|
| Sodium sulfite | 1.00 g |
| Ammonium dihydrogen phosphate | 1.00 g |
| Turpinal ® SL[1] | 0.12 g |
| Ascorbic acid | 0.40 g |
| L-Arginine | 1.00 g |
| p-Toluylenediamine · H$_2$SO$_4$ | 242.3 mg |
| 2-Methyl resorcinol | 50.2 mg |
| 4-Clororesorcinol | 48.6 mg |
| 2-Methylamino-3-amino-6-methoxypyridine | 3.5 mg |
| Vitamin B6 (pyridoxine · HCl) | as shown in Table 2 |
| Ammonia (25% aqueous solution) | to pH 8.4 |
| Water | 10.009 |

[1]1-Hydroxyethane-1,1-diphosphonic acid (INCI name: Etidronic Acid, Aqua (Water)) (COGNIS)

The dye precursors were dissolved in the water (heated to 50° C.) while the sodium sulfite, ammonium dihydrogen phosphate, Turpinal® SL, ascorbic acid and L-arginine were added. The pH was adjusted to 8.4 with ammonia.

| Mixture C (for coloring cream 2) | |
|---|---|
| Sodium sulfite | 0.40 g |
| Ammonium dihydrogen phosphate | 0.80 g |
| Turpinal ® SL[1] | 0.12 g |
| Ascorbic acid | 0.40 g |
| L-Arginine | 1.00 g |
| Rodol[2] 9R Base ® | 0.10 g |
| p-Toluylenediamine · H$_2$SO$_4$ | 528.0 mg |
| 2,4,5,6-Tetraaminopyrimidine · H$_2$SO$_4$ | 528.0 mg |
| 4-Amino-3-methylphenol | 864.0 mg |
| 4-Chlororesorcinol | 144.0 mg |
| 2,7-Dihydroxynaphthalene | 242.0 mg |

| Mixture C (for coloring cream 2) | |
|---|---|
| 2,6-Di(hydroxyethylamino)toluene | 66.0 mg |
| Vitamin B6 (pyridoxine · HCl) | as shown in Table 2 |
| Ammonia (25% aqueous solution) | to pH 8.6 |
| Water | 10.00 g |
| 2n HCl (aqueous solution) | 3.5 ml |

[1]1-Hydroxyethane-1,1-diphosphonic acid (INCI name: Etidronic Acid, Aqua (Water)) (COGNIS)
[2]6-Chloro-4-nitro-2-aminophenol (LOWENSTEIN)

The dye precursors were dissolved in the water heated to 50° C. to which 3.5 ml of an aqueous 2 n HCl solution had been added along with the sodium sulfite, ammonium dihydrogen phosphate, Turpinal® SL, ascorbic acid and L-arginine. The pH was adjusted to 8.6 with ammonia.

Coloring cream 1 was prepared by adding mixture B to 50 g of the emulsion (mixture A) and making up with water to 100 g. Coloring cream 2 was similarly prepared except that mixture C was used instead of mixture B.

B2) Coloring of the Fibers 50 ml of the coloring cream obtained in accordance with B1) was mixed with 40 ml of a 5% H$_2$O$_2$ solution and the mixture was applied to 5 cm long tresses of human hair (Naturweiβ, Kerling). After a contact time of 30 minutes at 32°, the hair was rinsed, washed with a standard shampoo and then dried.

The results are set out in Table 2.

TABLE 2

| Example | Coloring cream used | Quantity of pyridoxine · HCl | Shade obtained |
|---|---|---|---|
| 1.B.1 | 1 | 0.00 g | Medium ash blond |
| 1.B.2 | 1 | 0.20 g | Medium beige blond |
| 1.B.3 | 1 | 0.50 g | Medium beige blond |
| 1.B.4 | 1 | 1.00 g | Medium golden blond |
| 1.B.5 | 2 | 0.00 g | Brown-red |
| 1.B.6 | 2 | 1.00 g | Brown-copper red |

2. Demonstration of the Structuring Effect of Vitamin B6 when Applied Together with the Colorant A) Analysis Method Used: HP-DSC (High-Pressure Differential Scanning Calorimetry)

Thermoanalytical investigations are particularly suitable for characterizing two-phase systems to which human hair fibers as fibrous keratins with their crystalline α-helix component and amorphous matrix component also belong. On the one hand, glass transitions and aging behavior of the amorphous matrix can be investigated, on the other hand the melting behavior of the crystalline helical phase provides important information. Thermoanalytical studies were described for the first time in 1899. The first differential thermoanalyses (DTA) of protein fibers were carried out towards the end of the fifties (F. Schwenker, J. H. Dusenbury, Text. Res. J. 1963, 30, pages 800 et seq; W. D. Felix, M. A. McDowall, H. Eyring, ibid. (1963), 33, pages 465 et seq). In the following years, various thermoanalytical measuring techniques, such as DTA, HP-DTA (high-pressure DTA) and DSC (differential scanning calorimetry) were applied to keratin fibers, for example to investigate the phenomenon of supercontraction, α-β-phase transitions of the helices or denaturing processes. Recently, the method of HP-DSC was used to study keratin fibers, more particularly at the Deutsches Wollforschungsinstitut (German Wool Research Institute) in Aachen (F. J. Wortmann, H. Deutz, J. Appl. Polym. Sci. 1993, 48, pp. 137 et seq.). HP-DSC rules out the problems associated with pyrolytic effects which occur in conventional DSC and the problems with data acquisition and interpretation by which DTA is attended. DSC measurements are carried out on keratins which are encapsulated with water in commercially obtainable pressure-tight measuring capsules. In the keratin/water system, a high water vapor pressure from which the HP-DSC analysis derives builds up in the encapsulated steel crucibles on heating to >100° C. The crucial difference between the HP-DSC thermograms of human hair fibers and normal DSC thermograms is that the endothermal peaks which reproduce the transition point and the transition enthalpy are shifted by ca. 90° C. to lower temperatures. This derives from the fact that, after diffusing into the hair fibers, the water reduces protein stability by weakening and splitting hydrogen bridge bonds and salt bonds so that the "gluing temperature" of the keratins is reduced. If only hydrogen bridges and salt bridges are dissolved by the supercontracting agent, such as water, the thermal effect is reversible (supercontraction). However, the process becomes irreversible when covalent bonds, such as disulfide bridges for example, are split. This happens when human hair fibers are heated with water to >150° C. in pressure-tight capsules. The irreversible transition, interpreted as the transition of the α-helical regions in the proteins into a random state, results in endothermal peaks, the position of the peaks reproducing the transition point or even the denaturing point and their area reproducing the transition or denaturing enthalpy.

Accordingly, both structural and chemical states and changes in fiber keratins and particularly in human hair fibers can be detected by dynamic differential scanning calorimetry (DSC). Under precisely defined test conditions, the processes detectable by calorimetry in human hair fibers can be recorded in the form of thermograms and used in regard to peak positions, structures and areas as an indicator for influencing order/disorder transitions through changes in inner and/or outer parameters produced, for example, by cosmetic treatment of the hair fibers. In other words, information on the strength of or damage to human hair fibers can be obtained from the endothermal peaks recorded in the thermogram of human hair fibers on the basis of peak position (transition point) and peak area (transition enthalpy).

Detailed investigations into the influence of the cystine content on the denaturing of the α-helices in keratins have, for example, shown that the denaturing temperature (transition temperature) of the keratin increases linearly with the cystine content. The effect of the increased stability of the matrix region through the higher degree of crosslinking of the increased percentage of disulfide bridges in the matrix is that the transition of the helices embedded in this matrix is made difficult, resulting in an increase in the denaturing temperature. Conversely, a reduction in the denaturing temperature and above all in the denaturing enthalpy can generally be observed in human hair fibers treated by permanent waving or bleaching or coloring (H. Deutz, Doktorarbeit, RWTH Aachen 1993).

B) Procedure

Human hair (Alkinco 6634) was intentionally damaged by permanent waving (commercial product Poly Lock extra starke Dauerwelle; 40 mins. permanent waving, 10 mins. fixing). The pretreated hair was then colored with a coloring cream with different contents of pyridoxine.HCl. The denaturing temperatures of the colored hair samples was thermoanalytically determined by HP-DSC.

B1) Preparation of the Coloring Gel and Coloring of the Fibers

To produce the coloring gel, a mixture A and a mixture B were prepared.

| Mixture A: | |
|---|---|
| Kokoslorol ® C12–18[1] | 8.00 g |
| Edenor ® PK 1805[2] | 6.75 g |
| Texapon ® NSO-UP[3] | 3.50 g |
| Dehydol ® LS 2[4] | 10.10 g |
| Propylenglykol ®-1, 2-US | 6.75 g |
| Isopropanol | 16.50 g |

[1]$C^{12-18}$ fatty alcohol (INCI name: Coconut Alcohol) (COGNIS)
[2]Oleic acid (INCI name: Oleic Acid) (COGNIS)
[3]Lauryl ether sulfate, sodium salt (Ca. 27.5% active substance, pH 10–11.5) (INCI name: Sodium Laureth Sulfate) (COGNIS)
[4]C12–14 fatty alcohol + 2EO (INCI name: Laureth-2) (COGNIS)
[5]Propylene glycol (99.7%, INCI name: Propylene Glycol) (REININGHAUS CHEMIE)

The components of mixture A were mixed together at room temperature.

| Mixture B | |
|---|---|
| Sodium sulfite | 0.40 g |
| Ascorbic acid | 0.40 g |
| Monoethanolamine | 4.50 g |
| L-Arginine | 1.00 g |
| Gluadin ® W 40[1] | 1.00 g |
| Turpinal[2] SL ® | 0.20 g |
| p-Toluylenediamine · $H_2SO_4$ | 0.19 g |
| 2,4,5,6-Tetraaminopyrimidine · $H_2SO_4$ | 1.62 g |
| 4-Amino-3-methylphenol | 57.0 mg |
| 2-Methylresorcinol | 1.00 g |
| 1-(β-Hydroxyethylamino)-4-methyl-2-nitrobenzene | 0.10 g |
| Vitamin B6 (pyridoxineHCl) | quantity to obtain the content in the mixture used as shown in Table 3 |
| Water | 37.00 g |

[1]Wheat protein hydrolyzate (INCI name: Aqua (Water), Hydrolyzed Wheat Protein, Sodium Benzoate, Phenoxyethanol, Methylparaben, Propylparaben) (COGNIS)
[2]1-Hydroxyethane-1,1-diphosphonic acid (INCI name: Etidronic acid, Aqua (Water)) (COGNIS)
[3]6-Chloro-4-nitro-2-aminophenol · HCl (LOWENSTEIN DYES)

The coloring gel was prepared by adding mixture B to mixture A.

B2) Coloring and Analysis of the Hair Samples 50 ml of a coloring gel prepared in accordance with B1) were mixed with 40 ml of a 5% $H_2O_2$ solution (pH value of the mixture 9.5) and applied to 0.5 g of damaged human hair. After a contact time of 30 minutes at 32° C., the hair was rinsed and then dried. The active ingredients were then tested for restructuring effects by HP-DSC measurements. The denaturing temperatures obtained are listed in Table 3.

TABLE 3

| Example | Quantity of pyridoxine · HCl | Denaturing temperature [° C.] |
| --- | --- | --- |
| 2.1 | 0.00 g | 141.6 |
| 2.2 | 0.20 g | 141.7 |
| 2.3 | 0.50 g | 142.4 |
| 2.4 | 1.00 g | 143.0 |

The denaturing temperature of the uncolored, damaged reference hair sample was 147.2° C.

What is claimed is:

1. In a process for coloring keratin fibers, more particularly human hair, in which:
    optionally, a pretreatment preparation is applied to the fibers,
    a colorant M2 is then applied to the fibers, optionally having been mixed immediately before application to the fibers from:
        a component M2a containing at least one oxidation dye precursor of the primary intermediate type and/or an indole and/or indoline derivative and
        a component M2b containing an oxidizing agent and/or an enzyme,
        the colorant M2 and the colorant M2 being rinsed off the fibers after a contact time of from 5 to 30 minutes,
wherein said process comprises adding to at least one of the pre-treatment preparation or preparations M2a, M2b or M2 a compound of formula (I):

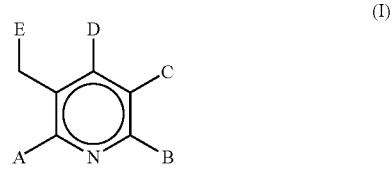

wherein
    A and B independently represent hydrogen, halogen, a $C_{1-4}$ alkyl group, a $C_{3-6}$ cycloalkyl group, a $C_{1-4}$ monohydroxyalkyl group, a $C_{2-4}$ oligohydroxyalkyl group, a $C_{1-4}$ aminoalkyl group, a group —OR or a group $NR^1R^2$;
    $R^1$ and $R^2$ independently represent hydrogen, a $C_{1-4}$ alkyl group or a $C_{1-4}$ monohydroxyalkyl group or $R^1$ and $R^2$ together with the nitrogen atom form a saturated ring;
    C represents a group —OR, $NR^1R^2$, —OP(O)(OR$^3$)$_2$, a $C_{1-4}$ monohydroxyalkyl group, a $C_{2-4}$ oligohydroxyalkyl group or a $C_{1-4}$ alkyl group;
    D represents a group —OR, a carboxy group, a $C_{1-22}$ alkoxycarbonyl group, a formyl group, a group —CH$_2$OR or a group —CH$_2$—NR$_2$,
    E represents a group —OR, —OP(O)(OR$^3$)$_2$, a $C_{1-4}$ monohydroxyalkyl group or a $C_{2-4}$ oligohydroxyalkyl group;
    —R represents hydrogen, a $C_{1-4}$ alkyl group, a $C_{1-22}$ acyl group, a hydroxy-$C_{2-22}$-acyl group, a $C_{2-10}$ carboxyacyl group, a $C_{3-10}$ oligocarboxyacyl group, an oligocarboxymonohydroxy-$C_{3-10}$-acyl group, an oligocarboxyoligohydroxy-$C_{3-10}$-acyl group, a $C_{3-8}$ cycloalkyl group, a $C_{1-4}$ monohydroxyalkyl group, a $C_{2-4}$ oligohydroxyalkyl group, an aryl group which may contain a hydroxy, nitro or amino group, a heteroaromatic group or a group —CH$_2$CH$_2$NR$^1$R$^2$, where $R^1$ and $R^2$ are as defined above; and
    —$R^3$ represents hydrogen or a $C_{1-5}$ alkyl group;
or any of the corresponding physiologically compatible salts thereof.

2. The process of claim 1, wherein one of the two groups A and B is hydrogen.

3. The process of claim 2, wherein the other of the two groups A and B is a $C_{1-4}$ alkyl group.

4. The process of claim 1, wherein C is a hydroxy group, a $C_{1-4}$ monohydroxyalkyl group or a $C_{2-4}$ oligohydroxyalkyl group.

5. The process of claim 1, wherein D is a hydroxymethyl group, a hydroxy group, a carboxy group or a formyl group.

6. The process of claim 1, wherein E is a hydroxy group or a group —OP(O)(OH)$_2$.

7. The process of claim 1, wherein formula (I) is pyridoxine.

* * * * *